United States Patent [19]

Knodell, Jr.

[11] Patent Number: 5,415,335

[45] Date of Patent: May 16, 1995

[54] SURGICAL STAPLER CARTRIDGE CONTAINING LOCKOUT MECHANISM

[75] Inventor: Thomas G. Knodell, Jr., Fort Worth, Tex.

[73] Assignee: Ethicon Endo-Surgery, Cincinnati, Ohio

[21] Appl. No.: 224,841

[22] Filed: Apr. 7, 1994

[51] Int. Cl.⁶ ............................................ A61B 17/068
[52] U.S. Cl. ...................................... 227/180; 227/8; 227/19
[58] Field of Search .................. 227/19, 180, 175, 176, 227/8, 178

[56] References Cited

U.S. PATENT DOCUMENTS

| | | | |
|---|---|---|---|
| 4,633,874 | 1/1987 | Chow et al. | 227/19 |
| 4,892,244 | 1/1990 | Fox | 227/8 |
| 4,955,959 | 9/1990 | Tompkins et al. | 227/178 |
| 5,129,570 | 7/1992 | Schulze et al. | 227/19 |
| 5,253,793 | 10/1993 | Green et al. | 227/8 |

Primary Examiner—Scott A. Smith
Attorney, Agent, or Firm—Paul A. Coletti

[57] ABSTRACT

Contained on a stapler cartridge there is at least one distal slot capable of accommodating at least one firing wedge or the knife blade which is thereby capable of moving through the distal slot. There is further contained at least one proximal slot capable of accommodating at least the one firing wedge or the knife blade. The firing wedge or knife blade is able to move into the proximal slot exclusively in a proximal direction. Once the firing wedge or the knife blade is moved into the slot, the firing wedge is no longer able to move distally, thereby locking end of proximal section of the stapler cartridge.

3 Claims, 4 Drawing Sheets

SURGICAL STAPLER CARTRIDGE CONTAINING LOCKOUT MECHANISM

FIELD OF THE INVENTION

This invention is generally related to a device for the prevention of the refiring of surgical staplers. More specifically, this invention is related to a device which contains a surgical stapler cartridge, and wherein the cartridge itself contains a lockout mechanism capable of preventing the refiring of a spent surgical stapler cartridge.

BACKGROUND OF THE INVENTION

Surgical staplers have become a very typical form of wound closure. These surgical staplers can provide various functions such as closing internal wounds, as well as suturing skin. In addition, staplers are useful in endoscopic purposes. Many of these surgical staplers have reloadable cartridges. These cartridges allow for the rapid reloading of the stapler during an operation. That is, the stapler can be used, the spent cartridge removed, and the surgical stapler reloaded with another cartridge to once again be ready for use.

A problem associated with the reloadable cartridges contained in surgical staplers commonly in use is the potential refiring of staplers containing spent cartridges. In other words, during the course of surgery it may be possible for the surgeon to use the stapler and then inadvertently not reload the stapler with an unused cartridge. The stapler is then inserted into the wound for use, and then fired. Of course, because the stapler cartridge is already spent, there will be no staples forthcoming from the stapler to fire another round of staples into tissue. This results in a delay while reloading the stapler cartridge. Also, if there is a knife mechanism associated with the stapler, the potential for wounding the patient exists.

In Fox, U.S. Pat. No. 4,892,244 there is described a stapler lockout mechanism which causes a barrier to be placed within the path of the firing mechanism. The Fox device prevents the refiring of the stapler once the stapler cartridge has been fired.

Schulze et al., U.S. Pat. No. 5,129,570 similarly describes a cartridge lockout mechanism device. It provides a cartridge which has a slot disposed within adjacent rows of staples, and wherein the slot extends substantially the entire length of the rows of staples. The stapler includes firing means for the staples and cutting means moveable in the slot. The stapler also includes a lockout mechanism for preventing movement of the cutting means in the slot. The lockout mechanism comprises a leaf spring disposed in the stapler and engages the bottom or lower surface of the knife mechanism forming the cutting means, to place the cutting means in a first position. In this first position, the cutting means is out of alignment with the slot contained in the stapler cartridge. In addition, there are means disposed on the cartridge for engaging the upper or top surface of the cutting means. The means for engaging the top surface of the cutting means depresses the leaf spring and moves the cutting means from its first position to a second position. In the second position, the cutting means is in alignment with the slot, so that the cutting means may move within the slot. After firing of the stapler, the means for engaging the top surface of the cutting means is moved, so that it no longer engages the cutting means. In this way, the cutting means is forced to remain in the first position, and therefore is out of alignment with the slot of the staple cartridge, so that firing the stapler is no longer possible.

It will be appreciated that various other lockout mechanisms have been disclosed in the art. However, all of these lockout mechanisms require movement by one or more moving members in the surgical stapler. None of the lockout mechanisms describe a stapler which contains a device inherently capable of locking out the cartridge without the lockout mechanism itself moving. It may be desirable to provide such a non-moving cartridge lockout mechanism.

SUMMARY OF THE INVENTION

Accordingly, it is an object of the invention to provide a surgical stapler with a lockout mechanism for preventing the refiring of a spent stapler cartridge.

It is another object of the invention to provide a surgical stapler with a lockout mechanism which is contained on the cartridge, and prevents the refiring of the spent stapler cartridge.

It is further an object of the invention to provide a lockout mechanism which is contained on a surgical stapler cartridge wherein the lockout mechanism is formed from non-moving parts.

Finally, it is an object of the invention to provide a lockout mechanism on the staple cartridge which not only has no moving parts, but which is actuated once the stapler cutting mechanism is moved a certain predetermined distance from its initial position.

These and other objects of the invention are described in the present surgical stapler which forms part of this specification. The surgical stapler provides a support mechanism and an actuation mechanism attached to the support mechanism. The actuation mechanism is connected to a knife blade and at least one stapler firing mechanism. There is contained a cartridge within which the knife blade and the staple firing mechanism are operable. The cartridge has at least one line of staples, and each of the staples are capable of being expelled from the cartridge during operation of the staple firing mechanism.

Contained on the cartridge there is at least one distal slot capable of accommodating at least one firing wedge or the knife blade which forms part of the staple firing mechanism, blade which is thereby capable of moving through the cartridge slot. There is further contained at least one proximal slot capable of accommodating at least the one firing wedge and the knife blade. The firing wedge or knife blade is able to move into the proximal slot exclusively in a proximal direction. Once the firing wedge or the knife blade is moved into the slot, the firing wedge is no longer able to move distally, thereby locking within a proximal section of the stapler cartridge. Therefore, once the firing wedge or the knife blade are moved into the proximal slot compartment contained on the cartridge, lockout occurs. This is accomplished without any moving parts on the surgical stapler lockout device. Rather, it is the motion of the stapler driver or the stapler knife which causes closing of the lockout mechanism in order to prevent refiring of the staples.

DESCRIPTION OF THE DRAWINGS

The objects of the present invention will be more fully described in the following drawings wherein.

DETAILED DESCRIPTION OF THE DRAWINGS

Figure 1:
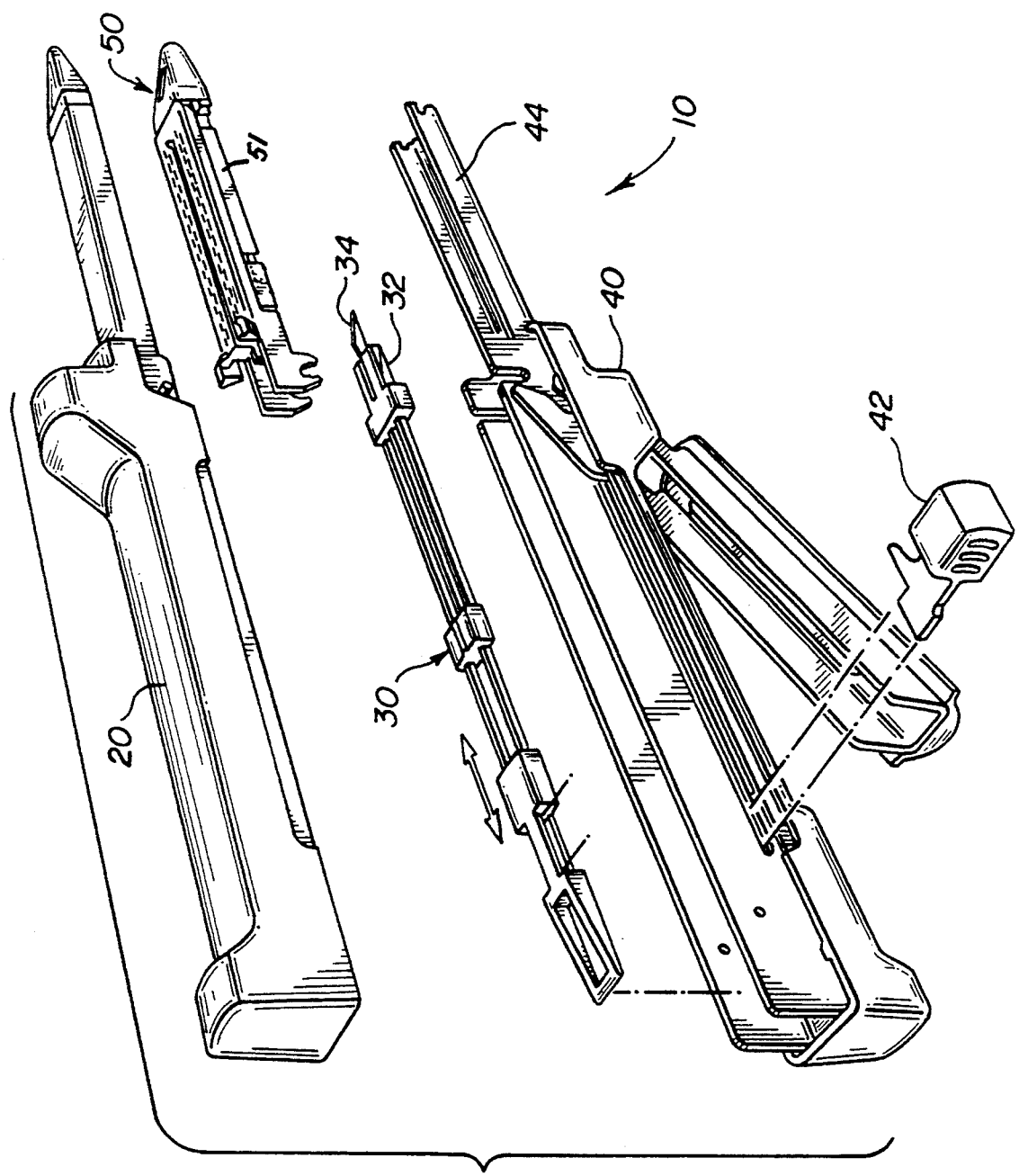
FIG. 1 is an exploded view in perspective of a surgical stapler loaded with a cartridge containing the lockout mechanism of the present invention.
Figure 2:
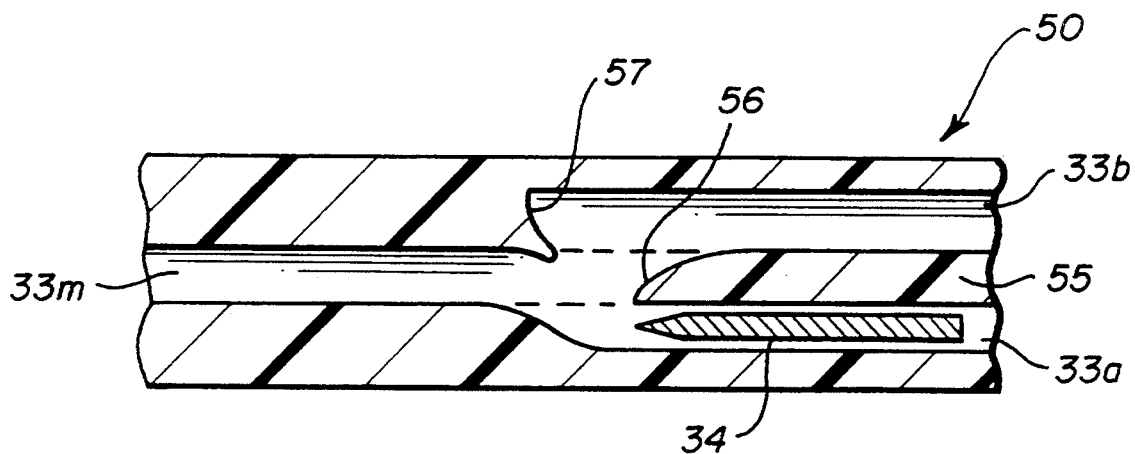
FIG. 2 is top view of the lockout mechanism of the present invention during actuation of the lockout mechanism at the beginning of the stroke of the surgical stapler.
Figure 3:
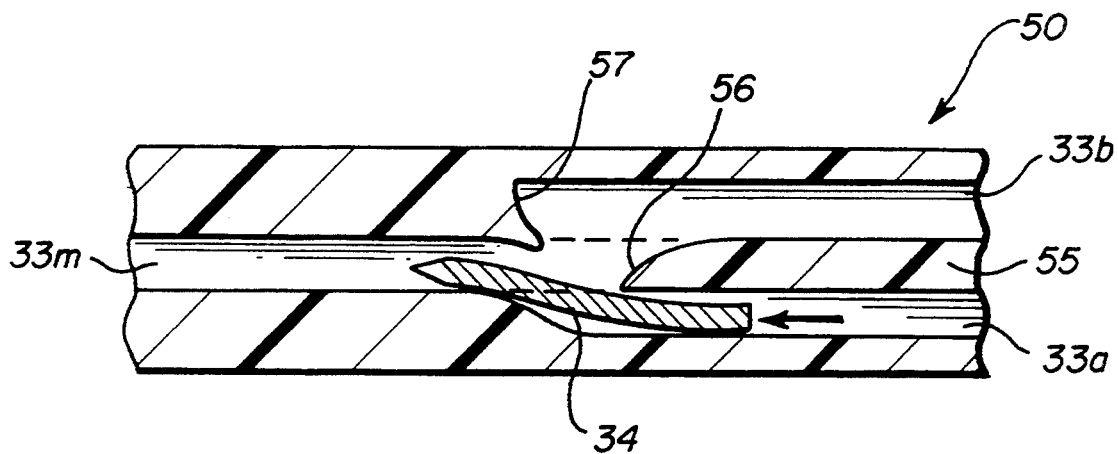
FIG. 3 is a view similar to FIG. 2 midway along the stroke of the stapler.
Figure 4:
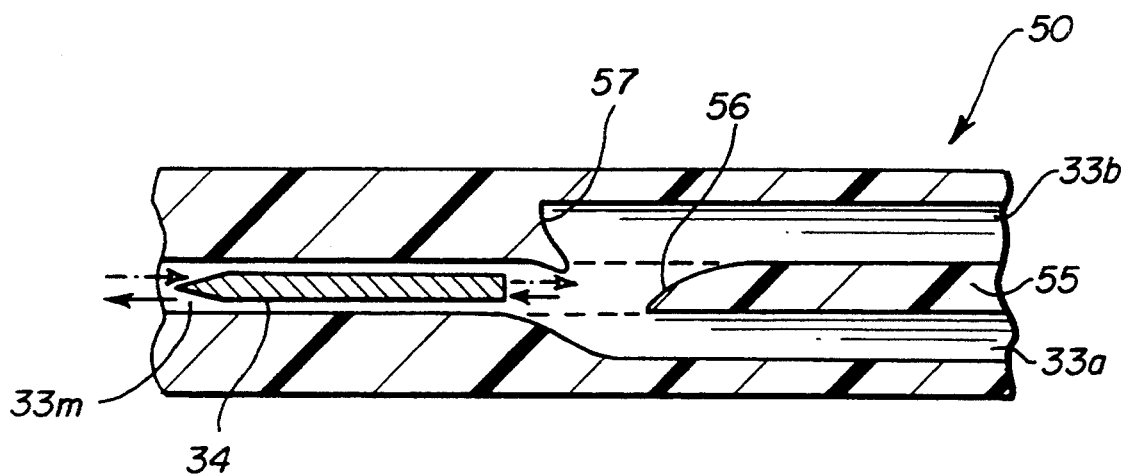
FIG. 4 is a view near the end of the stroke of the stapler.
Figure 5:
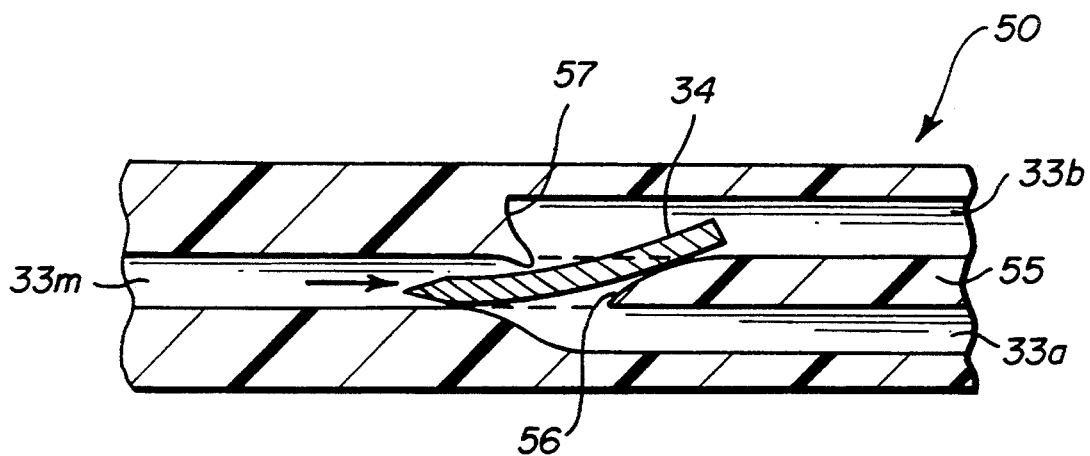
FIG. 5 is a view during the beginning of lockout in the stapler cartridge.

As seen in FIG. 1, a typical surgical stapler 10 has an upper jaw 20, firing means 30, a lower jaw 40 and a staple cartridge 50 which fits within the lower jaw 40. Firing means 30 generally comprises a pusher bar or firing wedge 32 as best seen in FIG. 1, and also contains a knife 34 which generally will be placed between the firing wedges 32. The firing wedges 32 sit within longitudinal slots 33 located on the staple cartridge 50. The staple cartridge 50 contains parallel sidewalls 51 which fit within the lower jaw channel 44.

As further seen in FIG. 1, a firing knob 42 activates the firing means 30 in order to send the firing wedges 32 through the staple cartridge 50. When the firing wedges 32 pass through the longitudinal slots 33 in the staple cartridge 50, the firing wedges 32 come into contact with drivers 52. These drivers are best seen in FIG. 1. The drivers 52 activate staples not shown so that the staples are ejected from the slots 53 seen in FIG. 1. On the upper jaw 20 there is an anvil 22 from which the staples are formed when they are driven through the slots 53.

Of course, alternate embodiments of surgical staplers with cartridges are possible. For instance, there is disclosed in Tompkins, incorporated herein by reference, U.S. Pat. No. 4,955,959 an alternate form of staple cartridge. Also, as further described in U.S. Pat. No. 5,170,925 endoscopic versions of a staple cartridge are possible. Of course, in either event, one merely needs the ability to remove the cartridge to replace it with an unfired cartridge containing new staples. What will be essential to this mechanism is the possibility of the lockout of the cartridge as further defined herein.

Figure 6:
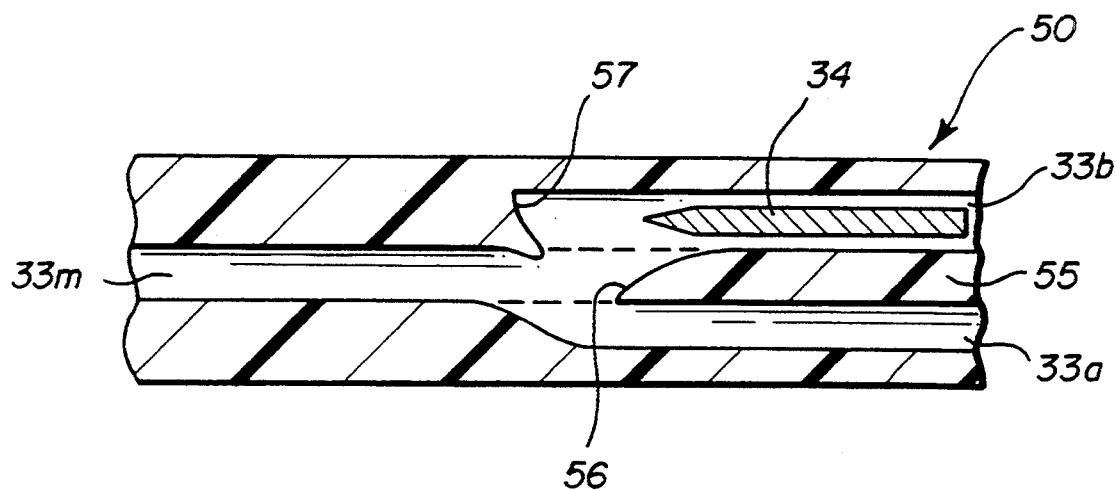
FIG. 6 is a view at lockout of the stapler.
Figure 7:
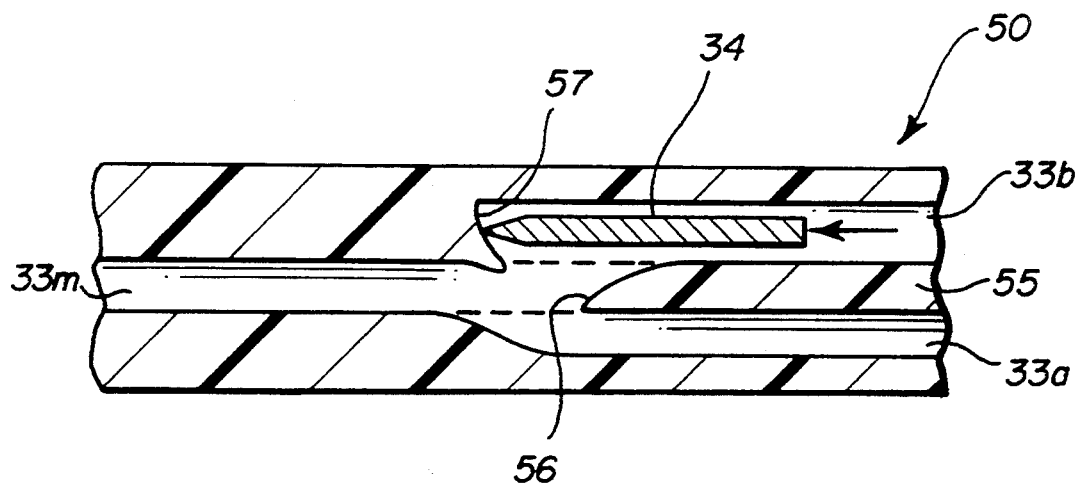
FIG. 7 is a view indicating lockout of the stapler cartridge.

Uniquely, the lockout mechanism of the present invention is not effected by any moveable member, as are the lockout mechanisms of the above described staplers. Rather, the lockout mechanism relies on a moveable member of the stapler, such as either the knife 34 or the firing wedges 32 moving and firing as is typical in a surgical stapler. Then, these moving members themselves effect lockout. As can be seen from the series of drawings in FIGS. 2-7, in this case the knife 34 moves from a initial loaded slot 33a through the cartridge 50. During the start of the firing sequence the knife 34 moves into the main knife slot 33m. Thereafter, the knife 34 is capable of moving through the cartridge 50 and while the stapler is firing staples simultaneously moving between firing wedges 32 and thereby cutting tissue while the staples are fired. Upon the return stroke, the knife 34 thereby contacts the island 55 formed as an injection molded piece of plastic between slots 33a and 33b. It will be noticed that the forward (distal) portion of the plastic island piece 55 contains a rounded and beveled edge 56 which causes the knife to be forced into a slot 33b. Thereafter, at the end of the return stroke, the knife 34 moves into slot 33b and, as seen in FIGS. 6 and 7 resides in slot 33b. Thereafter, upon an attempt to move the knife 34 distally from slot 33b, there is encountered a mechanical barrier 57 formed from in plastic or other suitable material from which the cartridge is formed.

It should be noticed that the knife 34 in this case must have substantial resilience in order to be able to move from one lateral position along the cartridge to another. However, with current manufacturing techniques as well as the current engineering designs, this hurdle is certainly capable of being overcome. In fact, in many instances it may be desirable to have a subtle amount of "play" in the knife 34 in order to enable the knife to pierce tissue when necessary.

In use, then, the operator must separate the handle halves 20, 40 of stapler 10, remove the spent cartridge 50, reposition knife 34 and wedges 32, load a new unused cartridge 50, and join halves 20, 40. Then, and only at that point, is the stapler 10 ready to re-use.

Furthermore, it should be noticed that the labyrinth effect in cartridge 50 created for passage of the knife may also be useful for, for instance, the firing wedges 32. Of course, with any of the firing devices, it will be necessary that they also have substantial amount of "play" in their lateral movement as well as the need for the cartridge 50 configured with a final locking position based on the positioning of the wedges 34. Naturally, it will be appreciated that all of these aspect of the invention are to be considered when reading and determining the invention from the attached claims.

I claim:

1. A surgical stapler comprising:
   a support mechanism;
   a knife blade and at least one staple firing wedge attached to an actuation mechanism;
   a cartridge through which said knife blade and said at least one staple firing wedge pass, said cartridge containing at least one line of staples, each of said staples capable of being expelled from said cartridge during operation of said staple actuation mechanism; and
   wherein said cartridge contains at least one distal slot for receiving at least one of said at least one firing wedge and said knife blade which thereby moves through said cartridge in a distal direction during the firing of said staples, and at least one proximal slot for receiving at least one of said at least one firing wedge and said knife blade from said at least one distal slot during movement of at least one of said at least one firing wedge and said knife blade in a proximal direction after the firing of said staples, said at least one proximal slot having a barrier at a distal end thereof for inhibiting the movement of at least one of said at least one firing wedge and said knife blade in a distal direction, whereby said at least one of said at least one firing wedge and said knife blade is retained within said proximal slot after said staples are fired.

2. The stapler of claim 1 wherein said at least one distal slot and said at least one proximal slot are parallel to one another along a portion of said cartridge.

3. The stapler of claim 2 wherein said at least one proximal slot is accessible from said at least one distal slot by a proximally directing wedge separating said at least one distal and at least one proximal slots.

* * * * *